United States Patent
Koh et al.

(10) Patent No.: US 10,770,172 B2
(45) Date of Patent: Sep. 8, 2020

(54) APPARATUS AND METHOD FOR HEALTH MANAGEMENT

(71) Applicant: SAMSUNG ELECTRONICS CO., LTD., Suwon-si (KR)

(72) Inventors: Young Jun Koh, Seoul (KR); Kak Nam Koong, Seoul (KR); Yeol Ho Lee, Anyang-si (KR); Myoung Hoon Jung, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 264 days.

(21) Appl. No.: 15/404,657

(22) Filed: Jan. 12, 2017

(65) Prior Publication Data
US 2018/0060530 A1    Mar. 1, 2018

(30) Foreign Application Priority Data
Aug. 25, 2016 (KR) .................. 10-2016-0108241

(51) Int. Cl.
*G16H 10/60* (2018.01)
*G16H 20/60* (2018.01)

(52) U.S. Cl.
CPC ............. *G16H 10/60* (2018.01); *G16H 20/60* (2018.01)

(58) Field of Classification Search
CPC ........ G16H 20/00; G16H 20/30; G16H 20/60; G06F 19/3475
See application file for complete search history.

(56) References Cited

U.S. PATENT DOCUMENTS

| | | | |
|---|---|---|---|
| 8,944,960 B2 | 2/2015 | Dugan | |
| 9,280,640 B2 | 3/2016 | Nusbaum et al. | |
| 2002/0133378 A1* | 9/2002 | Mault | A61B 5/0002 705/3 |
| 2004/0131227 A1* | 7/2004 | Bravomalo | G06Q 30/0269 382/100 |
| 2008/0021731 A1* | 1/2008 | Rodgers | A61B 5/1113 705/2 |
| 2013/0198214 A1* | 8/2013 | Hall | G06F 19/3475 707/758 |

(Continued)

FOREIGN PATENT DOCUMENTS

| | | |
|---|---|---|
| KR | 10-0481677 B1 | 4/2005 |
| KR | 10-2009-0033751 A | 4/2009 |

(Continued)

OTHER PUBLICATIONS

Denison et al., "Prevention and optimal management of sarcopenia: a review of combined exercise and nutrition interventions to improve muscle loss outcomes in older people", May 2015, Dovepress, pp. 859-869 (Year: 2015).*

(Continued)

*Primary Examiner* — John P Go
(74) *Attorney, Agent, or Firm* — Sughrue Mion, PLLC (57) ABSTRACT

An apparatus for health management includes an information collector configured to collect body composition information and characteristic information of a user, and a processor configured to determine a degree of muscle loss of the user based on the body composition information and the characteristic information of the user and provide a personalized health management program to the user based on the determined degree of muscle loss.

14 Claims, 7 Drawing Sheets

(56) References Cited

U.S. PATENT DOCUMENTS

| | | | |
|---|---|---|---|
| 2014/0172314 A1 | 6/2014 | Baarman et al. | |
| 2014/0242556 A1 | 8/2014 | Yoo et al. | |

FOREIGN PATENT DOCUMENTS

| | | | |
|---|---|---|---|
| KR | 10-2011-0130323 A | 12/2011 | |
| KR | 10-2012-0013817 A | 2/2012 | |
| KR | 10-2013-0142328 A | 12/2012 | |
| KR | 10-2015-0112234 A | 10/2015 | |
| KR | 10-2015-0136912 A | 12/2015 | |
| KR | 10-2015-0137225 A | 12/2015 | |
| KR | 10-1572687 B1 | 12/2015 | |
| KR | 10-2016-0000124 A | 1/2016 | |
| KR | 10-2016-0002456 A | 1/2016 | |

OTHER PUBLICATIONS

Calvani ("Current nutritional recommendations and novel dietary strategies to manage sarcopenia," J Frailty Aging. 2013; 2(1): 38-53 (Year: 2013).*

Gray, "Predicting sarcopenia from functional measures among community-dwelling older adults," AGE (2016) 38:22 (Year: 2016).*

Rubbieri et al., "Techniques for the diagnosis of sarcopenia", 2014, Clinical Cases in Mineral and Bone Metabolism, pp. 181-184 (Year: 2014).*

Taaffe et al., "Musculoskeletal health and the older adult", Journal of Rehabilitation Research & Development, Mar./Apr. 2000, 11 pages total, vol. 37, No. 2, VA Research and Development.

Terjung, "SSE #54: Muscle Adaptations to Aerobic Training", Sports Science Exchange, 2014, 6 pages total, Gatorade Sports Science Institute, Syracuse, NY.

Harridge et al., "Knee extensor strength, activation, and size in very in elderly people following strength training", Muscle Nerve, Jul. 22, 1999, 1 page total, Copenhagen Muscle Research Centre, Rigshospitalet, Copenhagen, Denmark.

Abe et al., "Age-related, site-specific muscle loss in 1507 Japanese men and women aged 20 to 95 years", Mar. 1, 2011, 6 pages total, pp. 145-150, Journal of Sports Science and Medicine, Japan.

Chen et al., "Relationship between muscle mass and muscle strength, and the impact of comorbidities: a population-based, cross-sectional study of older adults in the United States", BMC Geriatrics, 8 pages total, pp. 1-8, BioMed Central, 2013.

Estrada et al., "Functional Impact of Relative Versus Absolute Sarcopenia in Healthy Older Women", Nov. 2007, 8 pages total, vol. 55, No. 11, The American Geriatrics Society.

Goodpaster et al., "The Loss of Skeletal Muscle Strength, Mass, and Quality in Older Adults: The Health, Aging and Body Composition Study", Journal of Gerontology: Medical Sciences, Apr. 24, 2006, 6 pages total, p. 1059-p. 1064, vol. 61A, No. 10, The Gerontological Society of America.

Janssen et al., "Low Relative Skeletal Muscle Mass (Sarcopenia) in Older Persons Is Associated with Functional Impairment and Physical Disability", May 2002, 8 pages total, vol. 50, No. 5, The American Geriatrics Society.

Kim et al., "Prevalence of Sarcopenia and Sarcopenic Obesity in the Korean Population Based on the Fourth Korean National Health and Nutritional Examination Surverys", Journal of Gerontology: Medical Sciences, Mar. 19, 2012, 7 pages total, Oxford University Press.

Kim et al., "Sarcopenia of the Old Age", Jun. 10, 2015, 7 pages total, The Korean Academy of Clinical Geriatrics, Seoul, KR.

Lee et al., "Age Associated Changes in Body Mass Index and Body Fat Distribution", Oct. 9, 2003, J Korean Acad Fam Med, 7 pages total, vol. 24, No. 11.

Messier et al., "Menopause and sarcopenia: A potential role for sex hormones", Maturitas, 2011, 6 pages total, Elsevier.

Mitchell et al., "Sarcopenia, dynapenia, and the impact of advancing age on human skeletal muscle size and strength; a quantitative review", Frontiers in Physiology, Jul. 11, 2012, 18 pages total, vol. 3, Article 260, Derby, UK.

Ostchega et al., "Isokinetic Leg Muscle Strength in Older Americans and Its Relationship to a Standardized Walk Test: Data from the National Health and Nutrition Examination Survey 1999-2000", Isokinetic Knee Extensor Strength, Jun. 2004, 6 pages total, vol. 52, No. 6, The American Geriatrics Society.

Park, "Sarcopenia of the Old Age", Jan. 22, 2007, 8 pages total, Departments of Internal Medicine.

Rittweger et al., "Sprint and endurance power and ageing: an analysis of master athletic world records", Oct. 28, 2008, 7 pages total, p. 683-p. 689, Proceedings of The Royal Society.

Studenski et al., "The FNIH Sarcopenia Project: Rationale, Study Description, Conference Recommendations, and Final Estimates", Journals of Gerontology: Medical Sciences, Feb. 14, 2016, 12 pages total, p. 547-p. 558.

Tagliaferri et al., "Muscle and bone, two interconnected tissues", Ageing Research Reviews 21, 2015, 16 pages total, p. 55-p. 70, Elsevier.

* cited by examiner

APPARATUS AND METHOD FOR HEALTH MANAGEMENT

CROSS-REFERENCE TO RELATED APPLICATION(S)

This application claims priority under 35 U.S.C. § 119(a) to Korean Patent Application No. 10-2016-0108241, filed on Aug. 25, 2016, in the Korean Intellectual Property Office, the disclosure of which is incorporated herein by reference in its entirety.

BACKGROUND

1. Field

The exemplary embodiments disclosed herein relate to an apparatus and method for health management which provide a health management program using body composition information.

2. Description of Related Art

A non-personalized health management method provides an indiscriminate system which does not consider individuals' body information and body composition, and hence may have an insignificant effect and even an adverse effect. The indiscriminate system provides standardized exercise therapy and diet information to all users. Such systems are provided with a focus on management of body fat and body weight while not taking into account age, sex, or a degree of imbalance of body composition of individual users, and accordingly the effects of exercise therapy and diet suggested by the systems are insufficient and even there may be a risk of injury to the users due to an inadequate exercise therapy.

In addition, a user may manually select a type or intensity of exercise and a diet from an on-demand system using an application at any time needed and try to perform health management activities. However, because the user of the on-demand system selects the type or intensity of exercise and works out without knowing or barely knowing his or her physical characteristics, there is still a risk of injury, and the system without feedback to the user may be ineffective in motivating and encouraging the user to consistently perform the provided exercise and maintain a diet and may not be efficient enough for health management.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an exemplary embodiment, there is provided an apparatus for health management including: an information collector configured to collect body composition information and characteristic information of a user; and a processor configured to determine a degree of muscle loss of the user based on the body composition information and the characteristic information of the user and provide a personalized health management program to the user based on the determined degree of muscle loss.

The body composition information may include one or more of the following: muscle mass, body fat mass, body water mass and body mass index (BMI), and the characteristic information may include one or more of the following: muscle strength, physical strength, sex, age, height, weight, and body condition information.

The processor may include an analyzer configured to determine the degree of muscle loss as indicating one of pre-sarcopenia, sarcopenia, severe sarcopenia, and sarcopenic obesity by analyzing the body composition information and the characteristic information.

The analyzer may be configured to make a prediction regarding a change in a health condition of the user according to the determined degree of muscle loss and generate warning information based on the prediction.

The processor may include a program manager configured to generate the personalized health management program based on one or more of the following: the degree of muscle loss, a prediction of a change in a health condition of the user, and an evaluation result of a personalized health management program previously provided to the user.

The program manager may be further configured to select at least one of a standard health management program from a health management program database and the previously provided personalized health management program previously provided to the user and generate the personalized health management program by modifying the selected health management program.

The apparatus may further include a communicator configured to establish a communication channel with a health management server and receive the standard health management program from the health management server.

After the personalized health management program is provided to the user, the program manager may be configured to monitor an execution history of the personalized health management program and evaluate the personalized health management program based on the execution history.

The apparatus may further include a display configured to present muscle-loss-related information that includes at least one of the degree of muscle loss and the personalized health management program on a display area.

The display may be configured to present the muscle-loss-related information on a display area of the display based on visual information predefined according to the degree of muscle loss.

The display may be configured to present, on a first section of the display area, history information about changes in the degree of muscle loss and present, on a second section of the display area, detailed information that includes one or more items of information associated with a portion of the history information, the portion being selected by the user from the first section, and the one or more items of information may include body composition information, characteristic information, the degree of muscle loss, a prediction of a change in a health condition, the personalized health management program, and an evaluation of the personalized health management program.

The display may be configured to present an identification mark that indicates the portion of the history information selected by the user from the first section.

According to an aspect of another exemplary embodiment, there is provided a method for health management including: collecting body composition information and characteristic information of a user; determining a degree of muscle loss of the user based on the body composition information and the characteristic information of the user;

and providing a personalized health management program to the user based on the determined degree of muscle loss.

The body composition information may include one or more of the following: muscle mass, body fat mass, body water mass and body mass index (BMI), and the characteristic information may include one or more of the following: muscle strength, physical strength, sex, age, height, weight, and body condition information.

The determining of the degree of muscle loss may include determining the degree of muscle loss as indicating one of pre-sarcopenia, sarcopenia, severe sarcopenia, and sarcopenic obesity by analyzing the body composition information and the characteristic information.

The providing of the personalized health management program may include generating the personalized health management program based on one or more of the following: the degree of muscle loss, a prediction of a change in a health condition, and an evaluation result of a personalized health management program previously provided to the user.

The generating of the personalized health management program may include, in response to determining the degree of muscle loss, selecting at least one of a standard health management program from a health management program database and the previously provided personalized health management program previously provided to the user and modifying the selected health management program.

The providing of the personalized health management program may include, in response to providing the personalized health management program to the user, monitoring an execution history of the personalized health management program and evaluating the personalized health management program based on the execution history.

The method may further include displaying muscle-loss-related information that includes at least one of the degree of muscle loss and the personalized health management program.

The displaying of the muscle-loss-related information may include displaying the muscle-loss-related information on a display based on visual information predefined according to the degree of muscle loss.

Other features and aspects will be apparent from the following detailed description, the drawings, and the claims.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Figure 1:
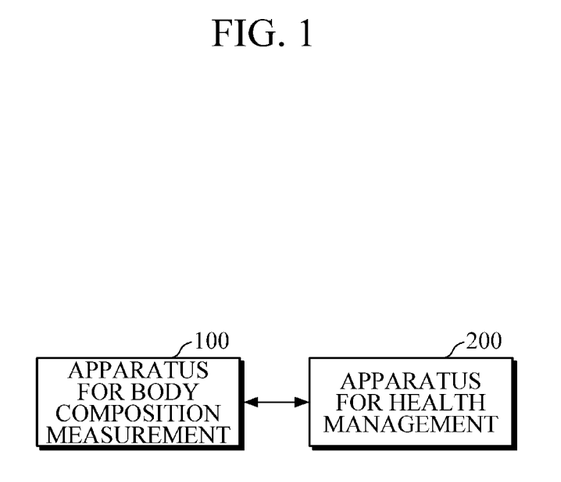
FIG. 1 is a block diagram illustrating an apparatus for body composition measurement and an apparatus for health management according to an exemplary embodiment.

FIG. 1 is a block diagram illustrating an apparatus for body composition measurement and an apparatus for health management according to an exemplary embodiment. The apparatus 100 for body composition measurement may include apparatuses for measuring dual energy x-ray absorptiometry (DEXA), magnetic resonance imaging (MRI), bio-electrical impedance analysis (BIA), and multi-frequency segmental bioelectrical impedance, but is not limited thereto, and may include various apparatuses capable of measuring body composition of a user.

The apparatus 100 may store measured body composition of the user and then transmit the information to the apparatus for health management upon request or transmit the information in real time over a wired or wireless network.

The apparatus 200 for health management may receive body composition information, analyze the received body composition information and characteristic information, and generate a personalized health management program. For example, the apparatus 200 may determine the user's body type based on a degree of imbalance of the body composition.

According to an exemplary embodiment, the apparatus 200 may determine a degree of muscle loss by analyzing the body composition information and characteristic information of the user, and provide a personalized health management program based on the determined degree of muscle loss. For example, the apparatus 200 for health management may select a standard health management program from a health management server or a health management program database based on the degree of muscle loss of the user, generate the personalized health management program by modifying the selected health management program and provide the program to the user.

The apparatus 200 in accordance with the present exemplary embodiment may be equipped as a hardware or software module in a wearable device, a terminal, such as a smartphone, a table PC, a desktop PC, laptop PC, etc., and a medical device, such as a blood pressure measurement device. In addition, the apparatus 200 may be implemented as an independent hardware device, but is not limited thereto, and may be implemented with various modifications according to the purpose of the application of the exemplary embodiment.

In addition, referring to FIG. 1, the apparatus 100 for body composition measurement is illustrated as being separated from the apparatus 200 for health management for convenience of description, but the apparatus 100 may be implemented in the form of a body composition measurement module and included in the configuration of the apparatus for health management.

Figure 2:
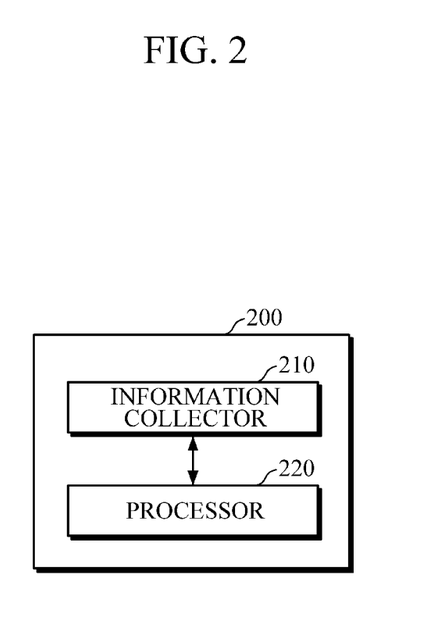
FIG. 2 is a block diagram illustrating an apparatus for health management according to an exemplary embodiment.

FIG. 2 is a block diagram illustrating an apparatus for health management according to an exemplary embodiment.

Referring to FIG. 2, the apparatus 200 for health management includes an information collector 210 and a processor 220. In this case, the information collector 210 and the processor 220 may include one or more processors and memories, and may be implemented as one or more modules by the combination of the processors and memories.

The information collector 210 may collect user information as basic information for generating user's personalized health management program. In this case, the user information may include the user's body composition information and characteristic information. For example, the user's body composition information may contain one or more of the following: muscle mass, body fat mass, body water mass, and body mass index (BMI), and the characteristic information may contain one or more of the following: muscle strength, physical performance, sex, age, height, weight and health condition information.

According to an exemplary embodiment, the information collector 210 may collect the user's body composition information measured by the apparatus for body composition measurement. For example, the information collector 210 may be connected with an external device over a wired or wireless network by controlling a communication module and acquire and collect the user's body composition information from the external device.

According to another exemplary embodiment, the information collector 210 may collect user's characteristic information. For example, the information collector 210 may be connected with an external device over a wired or wireless network by controlling a communication module and acquire the result of measuring muscle strength and physical performance of the user from the external device. In this case, the user's physical performance may be the result of measuring a short physical performance battery (SPPB), a gait speed, a timed up to go (TUG), and a jumping test.

In addition, the information collector 210 may store the collected body composition information and characteristic information of the user in a storage device. In this case, the storage device may include at least one of a flash memory, a hard disk, a micro type multimedia card, and a card type memory (e.g., SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, an optical disk, and the like. In addition, the storage device may be equipped in the apparatus 200 for health management, but is not limited thereto, or may be implemented as a hardware device which is connected with the apparatus 200 over a wired or wireless network.

The processor 220 may analyze the body composition information and characteristic information of the user and determine a degree of muscle loss of the user. Here, the degree of muscle loss may be a muscle mass related to age. For example, the processor 220 may compare an age-specific average muscle mass with the user's muscle mass and, if the user's muscle mass is less than the average muscle mass, determine the user's degree of muscle loss according to a degree of difference between the average muscle mass and the user's muscle mass.

In another example, the processor 220 may classify the user's degree of muscle loss into different stages by analyzing the body composition information and the characteristic information of the user. For example, the processor 220 may classify the user's degree of muscle loss based on one or more of the following: the user's muscle mass, muscle strength, and physical performance. In other words, if the user's muscle mass is less than the age-specific average muscle mass while the user's muscle strength and physical performance are within normal ranges, the processor 200 may determine that the user's degree of muscle loss indicates pre-sarcopenia. In addition, if the user's muscle mass is less than the age-specific average muscle mass and one of the user's muscle strength and physical strength falls below a normal range, the processor 220 may determine that the user's degree of muscle loss indicates sarcopenia, and if the user's muscle mass is less than the age-specific average muscle mass and both the user's muscle strength and physical performance fall below normal ranges, the processor 220 may determine that the user's degree of muscle loss indicates severe sarcopenia. However, the above classification of the degree of muscle loss is only an example, and the exemplary embodiments are not limited thereto, such that the degree of muscle loss may be classified based on various criterion.

In addition, in the case where it is determined that the user's degree of muscle loss is greater than a degree of muscle loss that indicates pre-sarcopenia while a ratio of the user's muscle mass to the user's fat mass exceeds a predetermined ratio (e.g., muscle mass:fat mass=2:1), the processor 220 may determine that the user's degree of muscle loss indicates sarcopenic obesity.

For example, the processor 220 may analyze the user's degree of imbalance of body composition and, if the degree of imbalance of the body composition exceeds a predetermined standard (e.g., if the ratio of the muscle mass to the fat mass exceeds 2:1), the processor 220 may determine that the user's body type is obese, and at this time, if it is determined that the user's degree of muscle loss is greater than the degree of muscle loss indicating the pre-sarcopenia, the processor 220 may determine that the user's body type is sarcopenic obese.

The processor 220 may generate a personalized health management program based on the determined degree of muscle loss. In this case, the health management program may be a personalized health management program which includes at least one of items including recommended exercise therapy, diets recommended, restaurants recommended, exercise places recommended and the monitoring history from previous programs.

For example, if the user's degree of muscle loss corresponds to sarcopenia, the processor 220 may generate a personalized health management program which includes an exercise therapy that recommends short-term and high intensive exercises (e.g., squats, pull-up, etc.) for developing fast-twitch muscles and a diet that recommends protein and vitamin containing food (e.g., egg whites, vegetables, etc.) which can help the recovery and synthesis of muscles.

According to another exemplary embodiment, the processor 200 may generate a personalized health management program based on the user's degree of muscle loss and the prediction of a change in a user's health condition. In this case, the prediction of change in a user's health condition may include a prediction of future change in a user's health condition when the user follows the health management program based on the current degree of muscle loss of the user or a prediction of future change in a user's health condition when the user does not conduct any actions. For example, the prediction may show a future degree of muscle loss based on the current degree of muscle loss. In other words, when the user's degree of muscle loss indicates pre-sarcopenia, the processor 220 may predict a change in a user's health condition (e.g., a progressive loss of muscle mass, a decline in muscle strength, an increase in risk accompanied by physical disability, etc.) when pre-sarcopenia is neglected.

In another example, when the user's degree of muscle loss is not less than a degree of muscle loss that indicates pre-sarcopenia, the processor 220 may predict the risk of pre-sarcopenia when the user's current health condition is neglected, based on the body composition information and the characteristic information.

According to still another example, the processor 220 may generate a personalized health management program based on one or more of the following: the user's degree of muscle loss, the prediction of a change in a user's health condition, and an evaluation result of a personalized health management program previously provided to the user.

For example, the processor 220 may provide the personalized health management program to the user, monitor an execution history of the personalized health management program and evaluate the program based on the execution history. If a predetermined length of time elapses (e.g., a week or a month) after the user's execution of the provided health management program, the processor 220 may generate an alarm for re-measuring a user's body composition information and the characteristic information and, in turn, evaluate the personalized health management program based on variations of the re-measured body composition information and characteristic information.

For example, the processor 220 may compare the previous body composition information and characteristic information with the re-measured body composition information and characteristic information, and if the muscle mass increases and muscle strength or physical performance is improved compared to the previous body composition information, the provided personalized health management program may be evaluated as adequate for the user. On the contrary, if the muscle mass does not change or even decreases, compared to the previous body composition information, the processor 220 may evaluate that the provided health management program is not adequate for the user.

If the provided health management program is evaluated as adequate for the user, the processor 220 may maintain the health management program, and if the program is evaluated as inadequate for the user, the processor 220 may modify the provided health management program to re-generate a personalized health management program. For example, the processor 220 may generate a personalized health management program in which a rate of intake nutrient contents is modified by adjusting the intensity of or the number of repetitions of exercise therapy or the diet in the previous personalized health management program.

The processor 220 may provide the generated personalized health management program to the user. For example, the processor 220 may provide the generated health management program to the user by presenting it on a display or may provide the user with the health management program through an external device via a communication module. In this case, the external device may be medical equipment for diagnosing the user's health condition, a printer for outputting a result, or a display device that displays the health management program. Besides, the external device may include a digital TV, a desktop computer, a mobile phone, a smartphone, a tablet computer, a laptop computer, a personal digital assistant (PDA), a portable multimedia player (PMP), a navigation system, an MP3 player, a digital camera, a wearable device, and the like, but the exemplary embodiments are not limited thereto.

In addition, the processor 220 may provide the generated personalized health management program to the user, modify the health management program based on an execution history of the health management program by the user and the variations in the body composition information, or the muscle mass and the physical performance which are re-measured after a predetermined length of time, and provide the modified health management program to the user.

Figure 3:
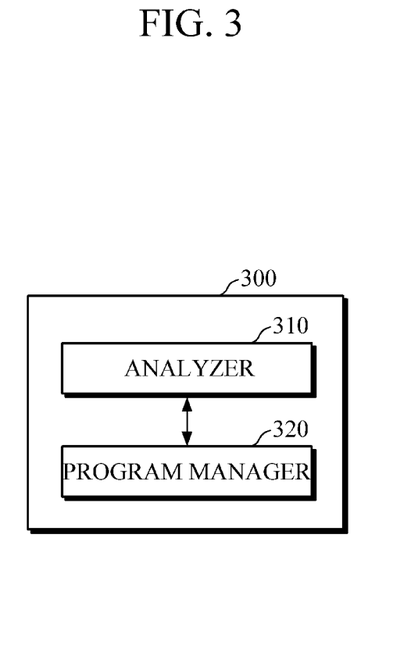
FIG. 3 is a block diagram illustrating a processor according to an exemplary embodiment.

FIG. 3 is a block diagram illustrating a processor according to an exemplary embodiment. Referring to FIG. 3, the processor 300 includes an analyzer 310 and a program manager 320.

The analyzer 310 may analyze collected body composition information and characteristic information of a user and classify a user's degree of muscle loss into different stages. Here, the classification into different stages may be performed when the user's degree of muscle loss falls below an age-specific average muscle mass based on the user's body composition information, and the classification refers to classifying the user's degree of muscle loss into different stages according to how much below various thresholds the user's level is. However, the exemplary embodiments are not limited to the above description, such that the user's degree of muscle loss may be classified based on one or more of the following: the muscle mass, muscle strength and physical performance of the user.

For example, when the user's muscle mass is below an age-specific average muscle mass while the muscle strength and the physical performance are within normal ranges, the analyzer 310 may classify the user's degree of muscle loss as pre-sarcopenia, when the user's muscle mass is below the age-specific average muscle mass while the muscle mass or the physical performance falls below a normal range, the analyzer 310 may classify the user's degree of muscle loss as sarcopenia, and when a user's muscle mass is below an age-specific average muscle mass and both the muscle strength and the physical performance also fall below normal ranges, the analyzer 310 may classify the user's degree of muscle loss as severe sarcopenia.

In another example, the analyzer 310 may determine the degree of muscle loss and a degree of obesity based on a ratio of the user's muscle mass to the user's fat mass. For example, when the user's degree of muscle loss is determined as being greater than a degree of muscle loss that indicates pre-sarcopenia and a ratio of muscle mass to fat mass exceeds a predetermined ratio (e.g., muscle mass:fat mass=2:1), the analyzer 310 may determine that the user's degree of muscle loss indicates sarcopenic obesity.

The analyzer 310 may predict a change in user's health condition once the user's degree of muscle loss is determined. In this case, the prediction of a change in a user's health condition may include a prediction of future change in a user's health condition when the user follows the health management program based on the current degree of muscle loss of the user or a prediction of future change in a user's health condition when the user does not conduct any actions. For example, in the case where the user's current degree of muscle loss is determined as indicating sarcopenia, the analyzer 310 may predict that the user's muscle loss will be "mitigated to a degree that would indicate pre-sarcopenia or a better condition" if the user manages his or her health condition according to the health management program, and the analyzer 310 may predict that the user would be "at risk of developing severe sarcopenia" if the user does not take any actions for his or her health condition.

The analyzer 310 may predict the change in the user's health condition and generate warning information based on the prediction. In this case, the warning information may include one or more of the following: the user's current muscle loss, the change in health condition which may occur when health management is performed according to the health management program, and the change in health condition which may occur when no any actions are taken. For example, when the analyzer 310 predicts that the user would be "at risk of developing severe sarcopenia" if specific actions are not taken, the analyzer 310 may generate warning information that includes information about a current degree of muscle loss which indicates sarcopenia and information about a "risk of developing severe sarcopenia" which is predicted for the case when no specific actions are taken.

When the user's degree of muscle loss is determined, the program manager 320 may select at least one of a standard health management program from a health management server or a health management program DB and a previous personalized health management program provided to the user. In this case, the standard health management program may be generated to be applicable in common to multiple individuals according to their body types. Alternatively, multiple users are classified into groups according to their body composition information and characteristic information, and the standard health management program may be a health management program that contains exercise programs and diets which are generated in advance for each user group.

In other words, the standard health management program may be a general health management program that does not reflect characteristics of each user, and may be, for example, a health management program that provides a balanced diet to a person of standard body type and an exercise therapy combining muscle exercises with aerobic exercises based on information about imbalance of body composition obtained by analyzing the user's body composition information.

Meanwhile, the previous personalized health management program may be a health management program that has been previously provided to the current user or a health management program that has been provided to another user having the similar body composition information and characteristic information as those of the current user.

The program manager 320 may generate a personalized health management program by modifying the selected health management program. For example, the program manager 320 may generate a personalized health management program based on one or more of the following: the user's degree of muscle loss, the prediction of a change in a user's health condition, and an evaluation result of a personalized health management program previously provided to the user.

In other words, when the user's degree of muscle loss is determined as indicating sarcopenia and it is predicted that the user would be "at risk of developing severe sarcopenia" if specific actions are not taken, by taking into account the fact that the user has sarcopenia, the program manager 320 may generate a health management program which includes a moderate intensity resistive exercise and a diet for recommending to intake meat or fish which contain creatine and theanine which are helpful in muscle strength enhancement and fatigue recovery.

In another example, in the case where the evaluation result of the previously provided health management program is "adequate", the program manager 320 may provide the same health management program again to the user, and in the case where the evaluation result is "inadequate", the program manager 320 may generate a new personalized health management program in which a rate of intake nutrient contents is modified by adjusting the intensity of or the number of repetitions of exercise therapy or the diet in the previous personalized health management program.

For example, a man in his seventies with sarcopenia who persistently works out and follows a diet based on a provided health management program may experience increase in muscle mass and physical performance. In this case, there may be a need of raising the level of difficulty of exercise therapy according to the increase in muscle mass and physical performance, and if the level of difficulty of exercise therapy is evaluated as needing to be raised, the program manager 320 may generate a personalized health management program by increasing the level of difficulty of the exercise therapy based on the evaluation result.

As such, by generating the personalized health management program, it is possible to increase health management efficiency, prevent any injuries, and promote the consistent use of the health management program.

The program manager 320 may provide the generated personalized health management program to the user. For example, the program manager 320 may provide the user with the generated health management program by presenting it on a display and may provide the user with the health management program through an external device via a communication module.

The program manager 320 may monitor an execution history of the personalized health management program provided to the user. For example, the program manager 320 may monitor whether the user has visited restaurants or exercise places (e.g., gyms) recommended by the health management program based on user location information and analyze a degree of execution of the provided health management program by calculating daily intake calories and calorie consumption. However, the exemplary embodiments are not limited to the above description, such that the program manager 320 may analyze the degree of execution of the health management program from meal information and exercise information that are manually input by the user. Here, the types of exercises and the diet consumed by the user may not be limited to the exercise program and the diet which are recommended by the health management program, and may be information about the actual exercises done by the user and the menus that the user actually has taken.

The program manager 320 may evaluate the personalized health management program based on the monitored execution history of the personalized health management program. For example, the program manager 320 may evaluate the provided health management program as "adequate" or "inadequate" based on the monitoring result of the user's execution history of the health management program, the number of executions of the health management program by the user, and a degree of satisfaction for diet recommendations.

According to an exemplary embodiment, the program manager 320 may generate alarm information based on the degree of execution of the personalized health management program provided to the user. For example, the program manager 320 may generate an alarm for re-measuring user's body composition information and the characteristic information when the user executes the provided personalized health management program during a specific period of time (e.g., a week or a month).

In addition, the program manager 320 may evaluate the personalized health management program based on variations of the re-measured body composition information and characteristic information. For example, the program manager 320 may compare the previous body composition information and characteristic information with the re-measured body composition information and characteristic information, and if the muscle mass increases, compared to the previous muscle mass, and muscle strength or physical performance is improved, the provided personalized health management program may be evaluated as adequate for the user. On the contrary, if the muscle mass does not change or even decreases, compared to the previous muscle mass, the provided health management program may be evaluated as inadequate for the user.

Figure 4:
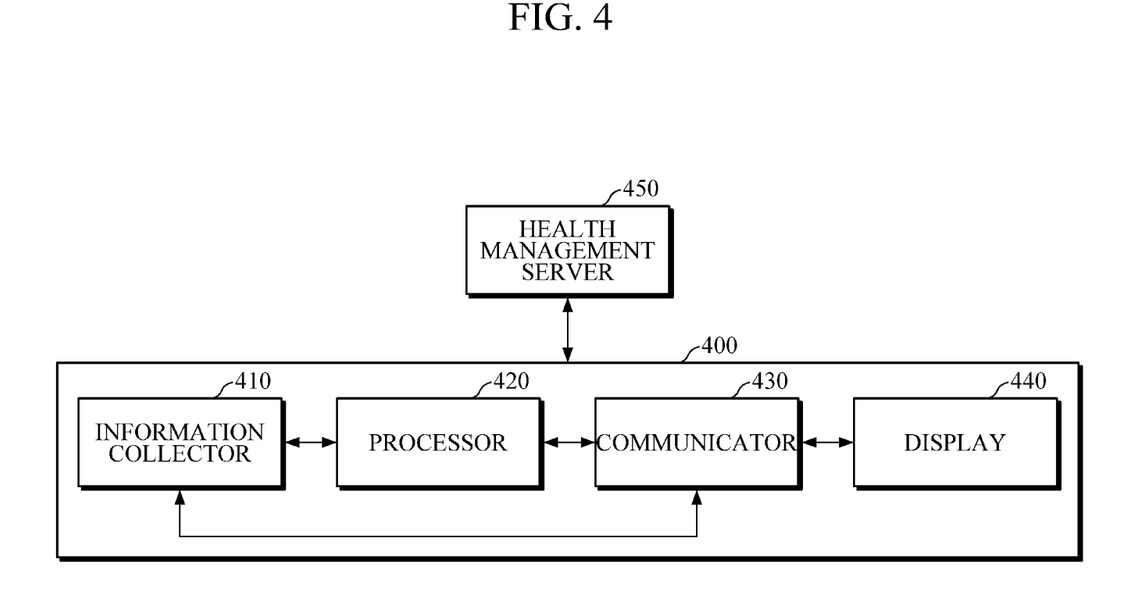
FIG. 4 is a block diagram illustrating an apparatus for health management according to another exemplary embodiment.

FIG. 4 is a block diagram illustrating an apparatus for health management according to another exemplary embodiment. Referring to FIG. 4, the apparatus 400 for health management includes an information collector 410, a processor 420, a communicator 430, and a display 440. In this exemplary embodiment, the information collector 410 and the processor 420 may be similarly configured as the information collector 210 and the processor 220 which are described with reference to FIG. 2, and hereinafter, descriptions will be provided with a focus on the configuration that has not been described above.

The communicator 430 may establish a connection with a health management server 450 under the control of the processor 420 and receive a standard health management program from the health management server 450. For example, the communicator 430 may transmit user information that contains at least one of body composition information and characteristic information of a user. In this case, the communicator 430 may receive a standard health management program that corresponds to the user information from the health management server 450.

However, the exemplary embodiments are not limited to the above description and in the case where the processor 420 includes the analyzer and the program manager, as described with reference to FIG. 3, the communicator 430 may receive the standard health management program from the health management server 450 over a wired or wireless network under the control of the program manager.

In addition, the communicator 430 may include one or more modules which communicate via Bluetooth, Bluetooth low energy (BLE) communication, a near field communication unit, wireless local area network (WLAN) communication, ZigBee communication, infrared data association (IrDA) communication, Wi-Fi direct (WFD) communication, ultra-wideband (UWB) communication, Ant+ communication, Wi-Fi communication, 3G communication, 4G communication, 5G communication, etc.

The display 440 may present muscle-loss-related information that includes at least one of a user's degree of muscle loss and a personalized health management program on a display area. For example, the display 440 may use visual information predefined according to the user's degree of muscle loss and present the muscle-loss-related information on the display. The display 440 may display the user's degree of muscle loss to be visually distinguishable, such that the user's degree of muscle loss which is not less than a degree that indicates pre-sarcopenia is "green" colored, the user's degree of muscle loss which indicates pre-sarcopenia is "yellow" colored, the user's degree of muscle loss which indicates sarcopenia is "orange" colored and the user's degree of muscle loss which indicates severe sarcopenia is "red" colored. However, the exemplary embodiments are not limited to the above description, such that the predefined visual information may include be implemented according to other methods for visually distinguishing between different degrees of muscle loss, for example, varying the colors, fonts, and text sizes.

Figure 5:
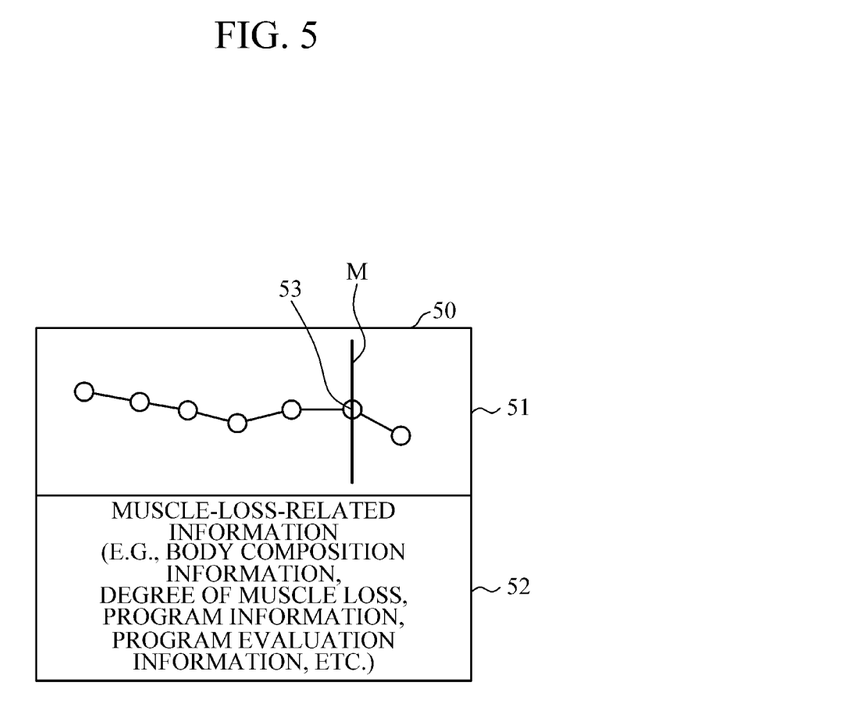
FIG. 5 is a diagram illustrating an example of displaying muscle-loss-related information on the display.

FIG. 5 is a diagram illustrating an example of displaying muscle-loss-related information on the display.

Referring to FIG. 5, the display 440 may divide a display area 50 into one or more sections, for example, a first section 51 and a second section 52 and display the muscle-loss-related information. For example, the display 440 may display a history of changes in muscle loss including the user's current muscle mass on the first section 51 of the display area 50 and detailed information that includes one or more items of information associated with the history of changes in muscle mass selected from the first section 51 on the second section 52 of the display area 50, wherein the information includes body composition information, characteristic information, a degree of muscle loss, prediction of change in health condition, a personalized health management program, and an evaluation of the personalized health management program.

In addition, the display 440 may display an identification mark M that indicates the history of changes in muscle loss selected by the user on the first section 51.

For example, the display 440 may display the currently selected history information 53 about changes in muscle loss on the first section 51 and display a mark M that indicates the history information 53. In FIG. 5, the mark M is illustrated as a vertical line, but is not limited thereto, and the mark may be displayed as a variety of shapes, such as a circle, a polygon, such as a rectangle, an arrow indicating a position, and the like. When the history of changes in muscle loss is displayed on the first section 51, the user may touch and select the history information 53 about a change in muscle loss at a specific time point or may align the desired history information 53 to the mark M by horizontally moving a graph, thereby selecting one portion of the history information 53 about a change in muscle loss. As such, when the user has selected one portion of the history information 53 about a change in muscle loss from the first section 51, the display 440 may display muscle-loss-related information associated with the selected history information about changes in muscle loss, for example, body composition information, a degree of muscle loss, a provided health management program, and information about program evaluation, on the second section 52.

Figure 6:
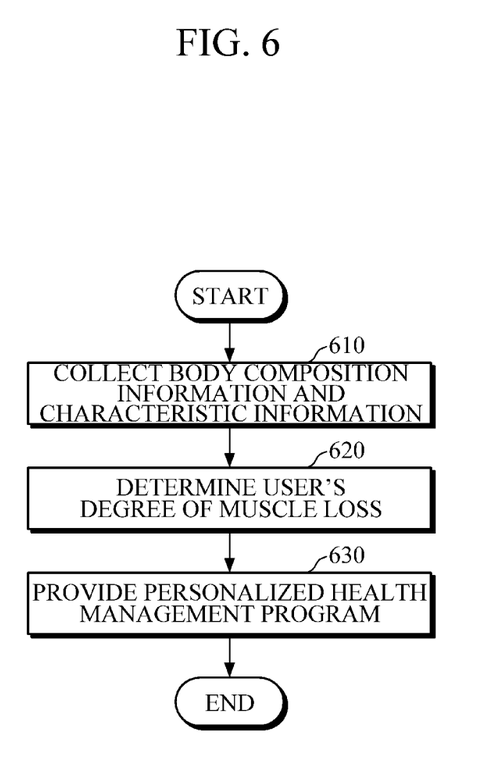
FIG. 6 is a flowchart illustrating a method for health management according to an exemplary embodiment.

FIG. 6 is a flowchart illustrating a method for health management according to an exemplary embodiment.

The method for health management shown in FIG. 6 may be one example of a method performed by the health management apparatus 200 of FIG. 2 for providing a health management program.

Referring to FIG. 6 in conjunction with FIG. 2, the apparatus 200 for health management collects user information as basic information for generating a health management program personalized to the user, as depicted in operation 610. In this case, the user information may contain the user's body composition information and characteristic information. For example, the user's body composition information may contain one or more of the following: muscle mass, body fat mass, body water mass, and BMI, and the characteristic information may contain one or more of the following: muscle strength, physical performance, sex, age, height, weight and health condition information.

According to an exemplary embodiment, the apparatus 200 may collect the user's characteristic information. For example, the information collector 210 may be connected with an external device over a wired or wireless network by controlling a communication module and acquire the result of measuring muscle strength and physical performance of the user from the external device. In this case, the user's physical performance may be the results of measuring a SPPB, a gait speed, a TUG, and a jumping test.

The apparatus 200 determines the user's degree of muscle loss by analyzing the collected body composition information and characteristic information, as depicted in operation 620. Here, the degree of muscle loss may be a muscle mass related to age.

According to an exemplary embodiment, the apparatus 200 may compare an age-specific average muscle mass with the user's muscle mass and, if the user's muscle mass is less than the average muscle mass, determine the user's degree of muscle loss according to a degree of difference between the average muscle mass and the user's muscle mass.

For example, the apparatus 200 may classify the user's degree of muscle loss into different stages by analyzing the body composition information and the characteristic information of the user. For example, the apparatus 200 may classify the user's degree of muscle loss based on one or more of the following: the user's muscle mass, muscle strength, and physical performance. In other words, if the user's muscle mass is less than the age-specific average muscle mass while the user's muscle strength and physical performance are within normal ranges, the apparatus 200 may determine that the user's degree of muscle loss indicates pre-sarcopenia.

In addition, if the user's muscle mass is less than the age-specific average muscle mass and one of a user's muscle strength and physical strength falls below a normal range, the apparatus 200 may determine that the user's degree of muscle loss indicates sarcopenia, and if the user's muscle mass is less than the age-specific average muscle mass and both the user's muscle strength and physical performance fall below normal ranges, the apparatus 200 may determine that the user's degree of muscle loss indicates severe sarcopenia. However, the above classification of the degree of muscle loss only an example, and the exemplary embodiments are not limited thereto, such that the degree of muscle loss may be classified based on various criterion.

Also, in the case where it is determined that the user's degree of muscle loss is greater than a degree of muscle loss that indicates pre-sarcopenia while a ratio of the user's muscle mass to the user's fat mass exceeds a predetermined ratio, the apparatus 200 may determine that the user's degree of muscle loss indicates sarcopenic obesity. For example, the apparatus 200 may analyze the user's degree of imbalance of body composition and, if the degree of imbalance of the body composition exceeds a predetermined standard (e.g., if the ratio of the muscle mass to the fat mass exceeds 2:1), the apparatus 200 may determine that the user's body type is obese, and at this time, if it is determined that the user's degree of muscle loss is greater than the degree of muscle loss indicating pre-sarcopenia, the processor 220 may determine that the user's body type is sarcopenic obese.

The apparatus 200 provides a personalized health management program based on the determined user's degree of muscle loss, as depicted in operation 630. For example, the apparatus 200 may select a standard health management program from a health management server or a health management program database based on the user's degree of muscle loss, generate the personalized health management program by modifying the selected health management program, and provide the program to the user.

In another example, the apparatus 200 may provide the generated personalized health management program to the user, modify the health management program based on an execution history of the health management program by the user and the variations in the body composition information, the muscle mass and the physical performance which are re-measured after a predetermined length of time, and provide the modified health management program to the user.

Figure 7:
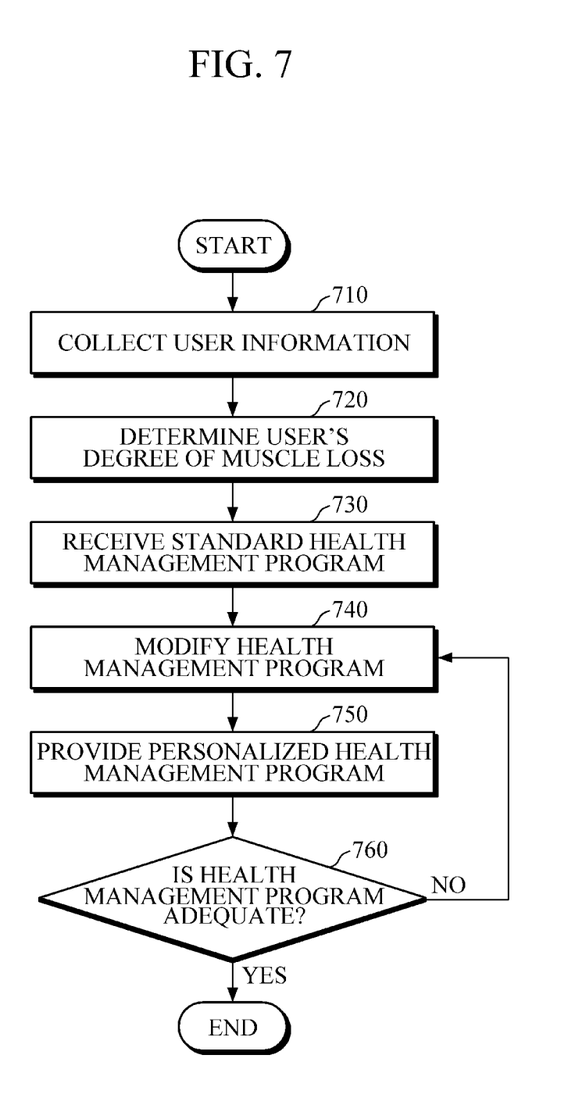
FIG. 7 is a flowchart illustrating a method for health management according to another exemplary embodiment.

FIG. 7 is a flowchart illustrating a method for health management according to another exemplary embodiment. The method shown in FIG. 7 may be one example of the method performed by the health management apparatus 400 of FIG. 4 for providing a health management program.

The apparatus 400 for health management collects user information as basic information for generating a health management program personalized to a user, as depicted in operation 710. In this case, the user information may contain a user's body composition information and characteristic information.

When the user information is collected, the apparatus 400 determines a user's degree of muscle loss, as depicted in operation 720. For example, the apparatus 400 may classify the user's degree of muscle loss based on one or more of the following: the user's muscle mass, muscle strength, and physical performance.

When the user's degree of muscle loss is determined, the apparatus 400 receives a standard health management program from a health management server, as depicted in operation 730. For example, the apparatus 400 may receive the standard health management program from the health management server from the health management server over a wired or wireless network according to a specific control signal. In this case, the standard health management program may be generated to be applicable in common to multiple individuals according to their body types. Alternatively, multiple users are classified into groups according to their body composition information and characteristic information, and the standard health management program may be a health management program that contains exercise programs and diets which are generated in advance for each user group.

The apparatus 400 modifies the standard health management program based on one or more of the following: the user's degree of muscle loss, the prediction of change in a user's health condition, and an evaluation result of a personalized health management program previously provided to the user, as depicted in operation 740.

For example, when the user's muscle mass is less than the age-specific average muscle mass and it is determined that the user has sarcopenia, the apparatus 400 may modify the standard health management program by changing the intensity of, and the number of repetitions of, exercises in the exercise program or adjusting a diet to recommend to intake meat or fish that contains creatine or theanine.

When a personalized health management program is generated by modifying the standard health management program, the apparatus 400 provides the generated personalized health management program to the user, as depicted in operation 750.

Thereafter, the apparatus evaluates whether the provided health management program is adequate or inadequate for the user, as depicted in operation 760. For example, the apparatus 400 may evaluate the provided health management program as "adequate" or "inadequate" based on the monitoring result of the user's execution history of the health management program, the number of executions of the health management program by the user, and a degree of satisfaction for diet recommendations.

However, the exemplary embodiments are not limited to the above description, such that if a predetermined length of time elapses (e.g., a week or a month) after the user's execution of the provided health management program, the apparatus 400 may generate an alarm for re-measuring a user's body composition information and the characteristic information and, in turn, evaluate the personalized health management program based on variations of the re-measured body composition information and characteristic information.

For example, the apparatus 400 may compare the previous body composition information and characteristic information with the re-measured body composition information and characteristic information, and if the muscle mass increases, compared to the previous muscle mass, and muscle strength or physical performance is improved, the provided personalized health management program may be evaluated as adequate for the user. On the contrary, if the muscle mass does not change or even decreases, compared to the previous muscle mass, the provided health management program may be evaluated as inadequate for the user.

According to an exemplary embodiment, in the case where it is determined that the health management program provided to the user is not adequate, the apparatus 400 may modify the health management program. For example, when the adequacy of the health management program has been evaluated, the apparatus 400 may modify the provided health management program and re-provide a personalized health management program.

For example, the apparatus 400 may lower a level of difficulty of exercise therapy in the provided standard health management program by taking into account a user's physical performance that is calculated as low or raise the level of difficulty of the exercise therapy by taking into account a user's physical performance that is calculated as high, thereby re-generating a personalized health management program, and provide the regenerated program to the user.

In other words, for example, a man in his seventies with sarcopenia who persistently works out and follows a diet based on a provided health management program may experience an increase in muscle mass and physical performance, and at this time, there may be a need to raise the level of difficulty of exercise therapy according to the increase in muscle mass and physical performance. Accordingly, if the level of difficulty of exercise therapy is evaluated as needing to be raised, the apparatus 400 may generate a personalized health management program by increasing the level of difficulty of the exercise therapy based on the evaluation result.

As such, by generating a personalized health management program, it is possible to increase health management efficiency, prevent any injuries, and promote the consistent use of the health management program.

The exemplary embodiments can be implemented as computer readable codes in a computer readable recording medium. Codes and code segments constituting the computer program can be easily inferred by a skilled computer programmer in the art. The computer readable recording medium includes all types of recording media in which computer readable data are stored. Examples of the computer readable recording medium include a ROM, a RAM, a CD-ROM, a magnetic tape, a floppy disk, and an optical data storage. Further, the recording medium may be implemented in the form of a carrier wave such as an Internet transmission. In addition, the computer readable recording medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for health management comprising:
   an information collector configured to collect body composition information and characteristic information of a user; and
   a processor configured to determine a degree of muscle loss of the user and a risk in a future health condition of the user based on the body composition information and the characteristic information of the user and provide a personalized health management program to the user based on the determined degree of muscle loss and the risk in the future health condition,
   wherein the risk in the future health condition comprises a risk of developing, if no further action is taken by the user, one of pre-sarcopenia, sarcopenia, severe sarcopenia, and sarcopenic obesity by analyzing the body composition information and the characteristic information,
   wherein the apparatus further comprises a display configured to:
      display, on a first section of a display area, a graph indicating a history of changes in the degree of muscle loss over time of the user, the history of changes including a current muscle mass of the user,
      in response to receiving a user selection of a portion of the graph, display, on the graph, an identification mark indicating the selected portion of the graph, the selected portion indicating information of a change in the degree of muscle loss at a specific time point, and display, on a second section of the display area, detailed information comprising one or more items of information associated with the change in the degree of muscle loss at the specific time point, and
      in response to receiving a user operation of horizontally moving a position of the identification mark on the graph, display on the second section of the display area, concurrently with the graph in the first section of the display area, detailed information comprising one or more items of information associated with a change in the degree of muscle loss at another time point corresponding to the position to which the identification mark is moved, and
   wherein the one or more items of information comprise at least one of the body composition information, the characteristic information, the degree of muscle loss, the risk in the future health condition, the personalized health management program, and an evaluation of the personalized health management program.

2. The apparatus of claim 1, wherein the body composition information comprises one or more of the following: muscle mass, body fat mass, body water mass and body mass index (BMI), and the characteristic information comprises one or more of the following: muscle strength, physical strength, sex, age, height, weight, and body condition information.

3. The apparatus of claim 2, wherein the processor comprises an analyzer configured to determine the degree of muscle loss as indicating the one of pre-sarcopenia, sarcopenia, severe sarcopenia, and sarcopenic obesity by analyzing the body composition information and the characteristic information.

4. The apparatus of claim 3, wherein the analyzer is configured to generate warning information based on the risk in the future health condition.

5. The apparatus of claim 1, wherein the processor comprises a program manager configured to generate the personalized health management program further based on an evaluation result of a personalized health management program previously provided to the user.

6. The apparatus of claim 5, wherein, the program manager is further configured to select at least one of a standard health management program from a health management program database and the previously provided personalized health management program previously provided to the user and generate the personalized health management program by modifying the selected health management program.

7. The apparatus of claim 6, further comprising a communicator configured to establish a communication channel with a health management server and receive the standard health management program from the health management server.

8. The apparatus of claim 5, wherein after the personalized health management program is provided to the user, the program manager is configured to automatically analyze a degree of execution of the personalized health management program based on user location information, and evaluate the personalized health management program based on the analyzed degree of execution of the personalized health management program.

9. A method for health management comprising:
collecting body composition information and characteristic information of a user;
determining a degree of muscle loss of the user and a risk in a future health condition of the user, based on the body composition information and the characteristic information of the user; and
providing a personalized health management program to the user based on the determined degree of muscle loss and the risk in the future health condition,
wherein the risk in the future health condition comprises a risk of developing, if no further action is taken by the user, one of pre-sarcopenia, sarcopenia, severe sarcopenia, and sarcopenic obesity by analyzing the body composition information and the characteristic information,
wherein the method further comprises:
displaying, on a first section of a display area of a display, a graph indicating a history of changes in the degree of muscle loss over time of the user, the history of changes including a current muscle mass of the user,
in response to receiving a user selection of a portion of the graph, displaying, on the graph, an identification mark indicating the selected portion of the graph, the selected portion indicating information of a change in the degree of muscle loss at a specific time point, and displaying, on a second section of the display area, detailed information comprising one or more items of information associated with the change in the degree of muscle loss at the specific time point, and
in response to receiving a user operation of horizontally moving a position of the identification mark on the graph, displaying on the second section of the display area, concurrently with the graph in the first section of the display area, detailed information comprising one or more items of information associated with a change in the degree of muscle loss at another time point corresponding to the position to which the identification mark is moved,
wherein the one or more items of information comprise at least one of the body composition information, the characteristic information, the degree of muscle loss, the risk in the future health condition, the personalized health management program, and an evaluation of the personalized health management program.

10. The method of claim 9, wherein the body composition information comprises one or more of the following: muscle mass, body fat mass, body water mass and body mass index (BMI), and the characteristic information comprises one or more of the following: muscle strength, physical strength, sex, age, height, weight, and body condition information.

11. The method of claim 9, wherein the determining of the degree of muscle loss comprises determining the degree of muscle loss as indicating the one of pre-sarcopenia, sarcopenia, severe sarcopenia, and sarcopenic obesity by analyzing the body composition information and the characteristic information.

12. The method of claim 9, wherein the providing of the personalized health management program comprises generating the personalized health management program based on one or more of the following: the degree of muscle loss, the risk in the future health condition, and an evaluation result of a personalized health management program previously provided to the user.

13. The method of claim 12, wherein the generating of the personalized health management program comprises, in response to determining the degree of muscle loss, selecting at least one of a standard health management program from a health management program database and the previously provided personalized health management program previously provided to the user and modifying the selected health management program.

14. The method of claim 12, wherein the providing of the personalized health management program comprises, after the personalized health management program is provided to the user, automatically analyzing a degree of execution of the personalized health management program based on user location information, and evaluating the personalized health management program based on the analyzed degree of execution of the personalized health management program.

* * * * *